(12) United States Patent
Cassidy et al.

(10) Patent No.: US 9,086,347 B2
(45) Date of Patent: Jul. 21, 2015

(54) CRYOPRESERVATION DEVICE WITH RETROFITTED ELECTRONIC TRACKING DEVICE

(75) Inventors: David E. Cassidy, Chelmsford, MA (US); Eric E. May, Norfolk, MA (US); Peter L. Minor, Wells, ME (US)

(73) Assignee: Provia Laboratories, LLC, Littleton, MA (US)

( * ) Notice: Subject to any disclaimer, the term of this patent is extended or adjusted under 35 U.S.C. 154(b) by 581 days.

(21) Appl. No.: 13/488,435

(22) Filed: Jun. 4, 2012

(65) Prior Publication Data

US 2013/0014526 A1 Jan. 17, 2013

Related U.S. Application Data

(60) Provisional application No. 61/492,905, filed on Jun. 3, 2011.

(51) Int. Cl.
*A01N 1/00* (2006.01)
*G01N 1/42* (2006.01)
*G01N 35/00* (2006.01)

(52) U.S. Cl.
CPC ............ *G01N 1/42* (2013.01); *G01N 35/00732* (2013.01)

(58) Field of Classification Search
CPC ....... B01L 3/54; B01L 3/545; B01L 2300/02; B01L 2300/021; B01L 2300/022; B01L 2300/024; A01N 1/0221; A01N 1/0252; A01N 1/0257; G01N 1/42; G01N 35/00732; G01N 35/00831
USPC .......................... 422/547, 554, 559, 560, 561; 435/283.1, 284.1, 307.1, 1.3
See application file for complete search history.

(56) References Cited

U.S. PATENT DOCUMENTS

| | | | | |
|---|---|---|---|---|
| 4,974,423 A * | 12/1990 | Pring | ............................. | 62/371 |
| 5,665,398 A * | 9/1997 | McCormick | .................. | 425/117 |
| 5,928,935 A * | 7/1999 | Reuss et al. | ................. | 435/288.1 |
| 5,935,848 A * | 8/1999 | Sputtek et al. | ............. | 435/307.1 |
| 6,126,313 A * | 10/2000 | Schiller | .......................... | 374/142 |
| 6,899,850 B2 * | 5/2005 | Haywood et al. | ............. | 422/547 |
| 2005/0069861 A1* | 3/2005 | Zimmermann et al. | ........ | 435/1.1 |
| 2006/0154232 A1* | 7/2006 | Degel et al. | ........................ | 435/2 |
| 2009/0029341 A1* | 1/2009 | Fuhr et al. | ...................... | 435/1.3 |

* cited by examiner

*Primary Examiner* — Jill Warden
*Assistant Examiner* — Dwayne K Handy

(57) ABSTRACT

The present invention is a cryopreservation device that has the ability to track and record preserved specimens using an integrated electronics system. The cryopreservation device stores specimens within a preservation chamber. A sealing cap encloses the preservation chamber. The integrated electronics system is embedded within a base attachment. The base attachment can be retrofitted into the cryopreservation device using a mechanical locking system and a recessed surface and cavity within the cryopreservation device. The mechanical locking system secures the base attachment into the cryopreservation device using multiple spring-loaded barbs and locking receptacles. The base attachment inserts within the recessed surface and cavity. The integrated electronics system uses a control block to operate a plurality of sensors and to attain time dependent specimen data. The specimen data is saved within a storage device. The specimen data can be retrieved without physically connecting to the integrated electronics system using a communication device.

16 Claims, 16 Drawing Sheets

CRYOPRESERVATION DEVICE WITH RETROFITTED ELECTRONIC TRACKING DEVICE

The current application claims a priority to the U.S. Provisional Patent application Ser. No. 61/492,905 filed on Jun. 3, 2011. The current application filed in U.S. Jun. 4, 2012 while Jun. 3, 2012 was on a weekend.

FIELD OF THE INVENTION

The present invention relates generally to an apparatus for a tracking device in cryogenic temperatures. More particularly, the present invention pertains to the tracking and record keeping of biological specimens that are stored at cryogenic temperatures.

BACKGROUND OF THE INVENTION

Modern tracking and record keeping systems used in cryogenics rely on adhesive labeling, paper tags and other similar labels or tags. At extremely low, cryogenic temperatures however, such labels and tags can easily become disconnected from the specimen or the surface that they are attached to. Invaluable information can easily be lost if the tracking and record systems fail to operate as intended. Specimens can even be accidently thawed if the specimens are poorly tracked. In the instances that the specimens need to be thawed and refrozen for a particular purpose, proper tracking and recording systems are still needed since this is an important part of determining the viability of the specimen. Although tracking and recording systems that function properly at cryogenic temperatures are available, they are expensive and often deemed unnecessary. The specimens contained within their preservation devices that have poor tracking and record keeping systems can have their well-being jeopardized. The object of the present invention is to provide a reusable and cost-effective cryopreservation device with a retrofitted electronic tracking device.

The present invention is a component that mounts onto a cryopreservation device. Electronics are integrated into a portion of the device so that a unique identification code and/or specimen data can be read without the use of adhesive labels or paper tags. The present invention is designed in a specific manner to be retrofitted onto existing cryopreservation devices. The present invention implements data storage into its retrofitted design that has the ability to be reused by simply being replaces or also to remain and receive additional memory. The present invention further implements electronics that are designed to operate at cryogenic temperatures.

DETAIL DESCRIPTIONS OF THE INVENTION

All illustrations of the drawings are for the purpose of describing selected versions of the present invention and are not intended to limit the scope of the present invention.

The present invention is a cryopreservation device 1 that can retrofit an integrated electronics system 3 into its embodiment. This is shown through FIG. 1-FIG. 14. Four primary components provides the present invention with ability to store specimens in a cryogenic environment while also being able to record desired parameters such as temperature, pressure, and humidity of this environment on a specimen-by-specimen basis. These four chief components include a cryopreservation device 1, a sealing cap 4, a base attachment 2 and an integrated electronics system 3. The cryopreservation device 1 in tandem with the sealing cap 4 should provide the present invention with the ability to preserve specimens at cryogenic temperatures and to protect the specimens from being contaminated. The integrated electronics system 3 contains the recording and tracking capability of the present invention. Specimen data is recorded so that the viability of the specimens being stored within the cryopreservation device 1 can be monitored. An individual should be capable of retrieving this specimen data without removing the cryopreservation device 1 from its cryogenic environment. The integrated electronics system 3 is contained within the base attachment 2. The present invention retrofits the base attachment 2 into the cryopreservation device 1. This is provided by a recessed surface and cavity within the structure of the cryopreservation device 1. A mechanical locking system keeps the base attachment 2 semi-permanently secured to the cryopreservation device 1. Additional components are also provided so that conventional tracking and recording methods can be maintained.

Figure 15:
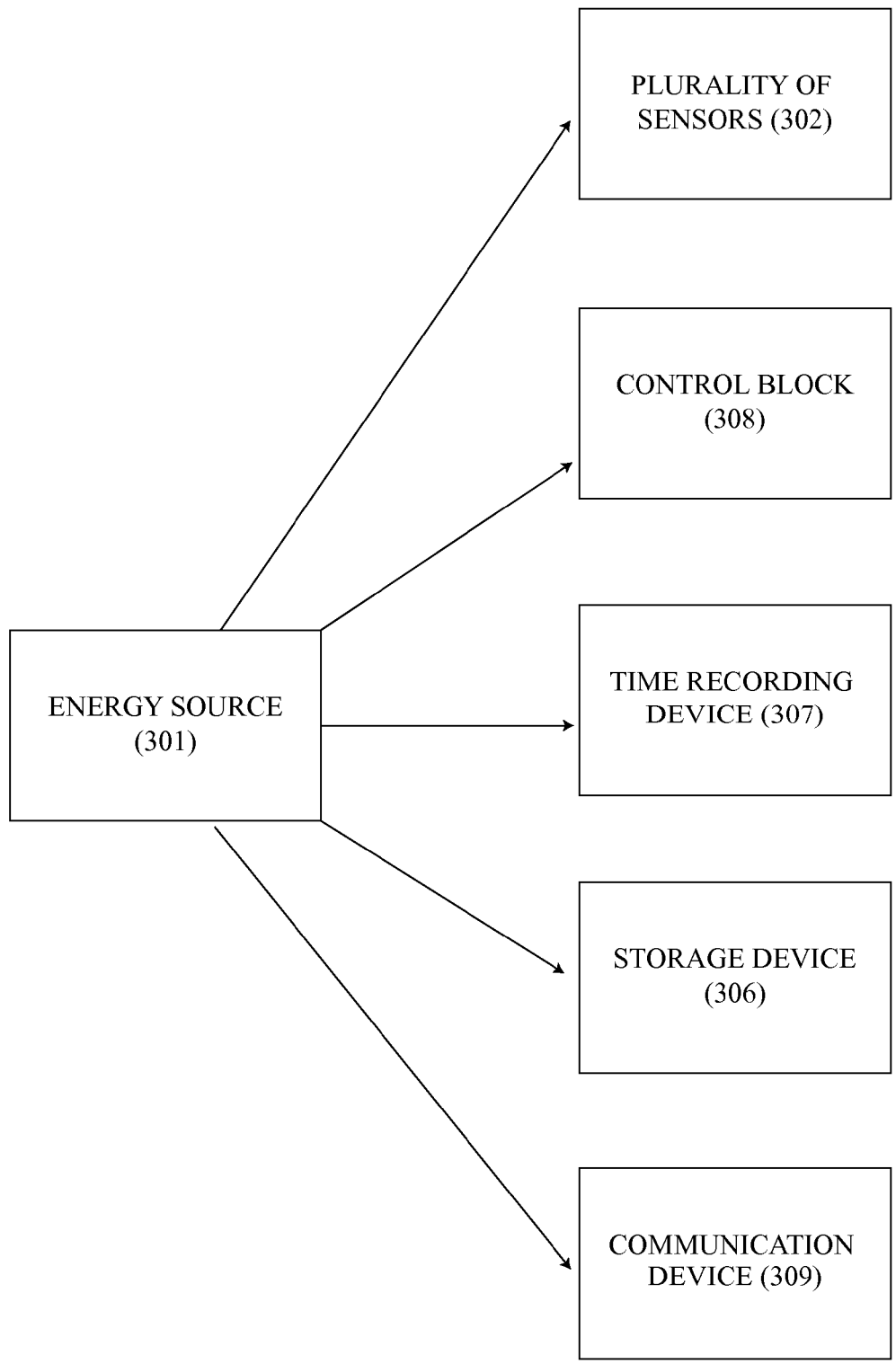
FIG. 15 is a diagram illustrating the electrical connections of the integrated electronics system.
Figure 16:
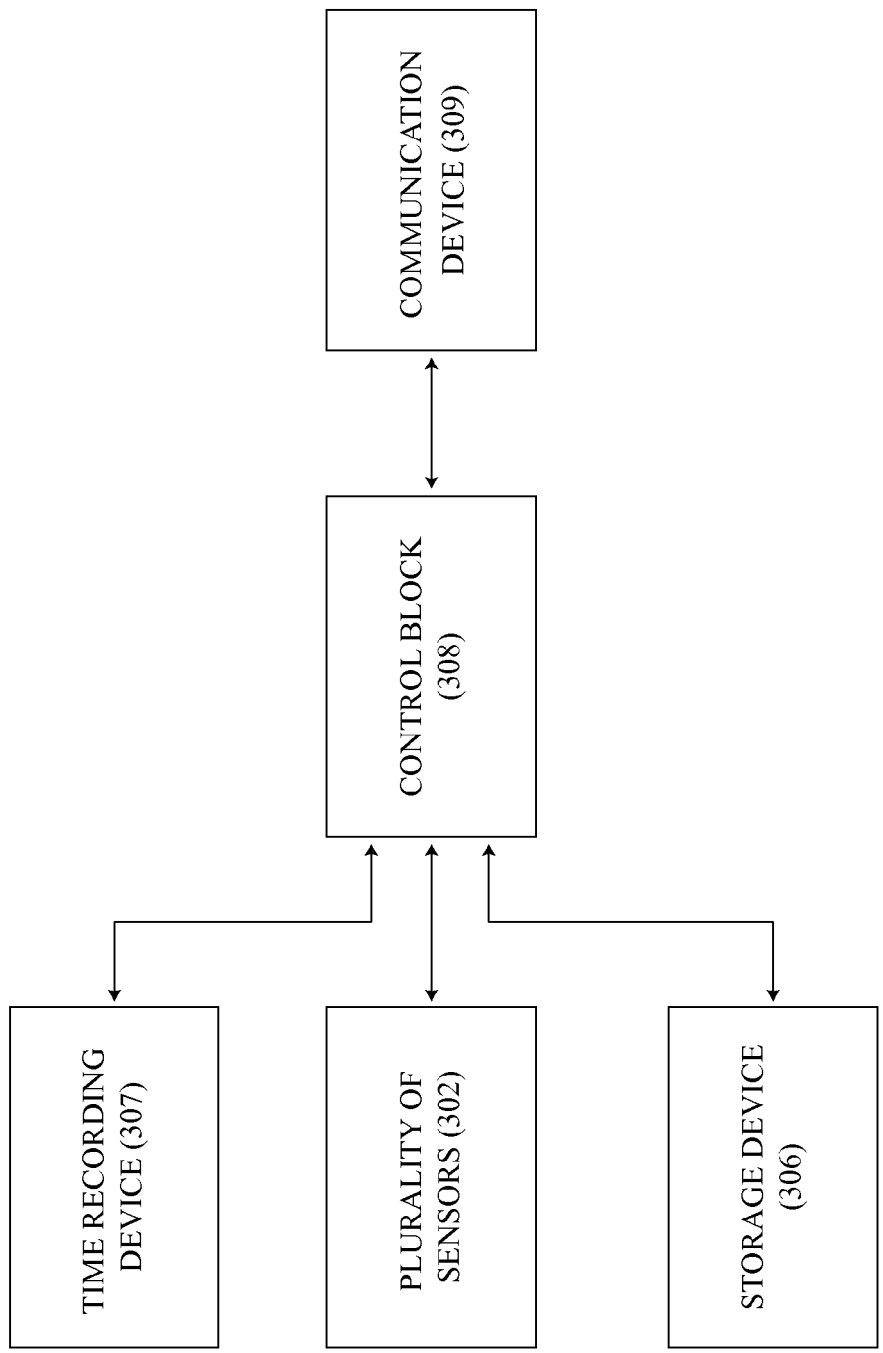
FIG. 16 is a diagram illustrating the function of the control block.

The electrical connections of the integrated electronics system 3 are delineated in FIG. 15. The integrated electronics system 3 comprises an energy source 301, a plurality of sensors 302, a data storage device 306, a time recording device 307, a control block 308, and a communication device 309, wherein the plurality of sensors 302 includes a temperature sensor 303, a humidity sensor 305 and a pressure sensor 304. Additional sensors may also be included and the present invention should not be limited to solely using a temperature sensor 303, a humidity sensor 305 or a pressure sensor 304. The tracking and recording ability of the present invention is attained by the integrated electronics system 3. The preferred embodiment of the energy source 301 is a battery that can supply power to all electronics within the integrated electronics system 3. The energy source 301, the data storage device 306, the time recording device 307, the communication device 309 and each of the plurality of sensors 302 are electrically connected to the control block 308. The electrical signals that are sent throughout the integrated electronics system 3 are appropriately directed by the control block 308, so that the integrated electronics system 3 can operate properly. This is generally delineated in FIG. 16. Each of the plurality of sensors 302 should communicate with the control block 308, time recording device 307, and the data storage device 306. For example, the temperature sensor 303 should be able to acquire data related to the current temperature and this data should be sent as an electrical signal by the control block 308 to the data storage device 306. The control block 308 may also need to sync the plurality of sensors 302 with the time recording device 307 in order to reliably track and deliver this data to the data storage device 306. The control block 308 is essentially the electronic controller of the integrated electronics system 3. Similarly, the pressure sensor 304 and the humidity sensor 305 should coincide with the time recording device 307, the data storage device 306 and the control block 308 so that the data and information from these sensors are properly tracked and recorded as well. The preferred embodiment of the communication device 309 is a radiofrequency identification (RFID) device that can transfer data from the data storage device 306 to another device that is not electrically connected to the integrated electronics system 3; however, any similar technology may be provided to achieve this function and the communication device 309 should not be limited to being an RFID device. It is important to attain the data from the integrated electronics system 3 without having to physically connect to the data storage device 306 because the integrated electronics system 3 is embedded within the base attachment 2.

Drastic changes in the environment of cryopreservation device can be monitored by retrieving the specimen data from the storage device 306. The viability of the preserved specimens can be determined from the specimen data. The viability of a specimen is usually dependent on these parameters: temperature, pressure, and humidity. If a specimen is thawed and refrozen repeatedly, or even once, the specimen may render erroneous data during an experiment. Conventional cryogenic storage containers monitor the temperature, pressure, and humidity within such a cryogenic storage as a whole. Therefore, the viability parameters may appear sufficient, yet it is possible that a specimen within the cryogenic storage container may have already deteriorated. Clearly, this is undesirable, and it is difficult to monitor such changes in the environment on a specimen-by-specimen basis—thousands of specimens may be cryogenically stored together. Routine checks of the specimens being preserved by the cryopreservation device 1 can easily be conducted by implementing the present invention because the specimen data can be directly attained through the communication device 309 without needing to remove the specimens from its cryogenic environment. This capability ensures that experiments and tests on specimens retrieved from the cryopreservation device 1 render useful results. Specimens that are no longer in good condition can also be easily pinpointed and discarded from the cryopreservation device 1 because only the specimen data needs to be analyzed and not the specimen, as aforementioned.

As is shown is shown by FIG. 5-FIG. 10 the cryopreservation device 1 comprises a first surface 5, a second surface 6, a first recessed surface 7, a preservation chamber 8, a receiving shell 11, a first locking receptacle 16, a second locking receptacle 17, a plurality of latching receptacles 18, and a plurality of clips 19. Essentially, the specimen preservation functionality is provided by the preservation chamber 8, wherein the preservation chamber 8 further comprises a chamber thread 9, a plurality of inner splines 10, and a chamber cavity 43. The preservation chamber 8 is positioned atop the first surface 5. The chamber thread 9 should enwrap the preservation chamber 8 helically so that the sealing cap 4 can be tightened to enclose the chamber cavity 43. Within the chamber cavity 43 are the plurality of inner splines 10. The plurality of inner splines 10 should be circumferentially positioned around the inner walls of the chamber cavity 43. These inner splines 10 keep specimen(s) positioned appropriately within the preservation chamber 8. The retrofitting capability of the cryopreservation device 1 is provided by the first recessed surface 5 and the receiving shell 11, wherein the receiving shell further comprises a first shell wall 12, a second shell wall 13, a lock indication arrow 42, a third locking receptacle 14, and a receiving cavity 15. The receiving shell 11 is positioned atop the first surface 5, adjacently to the preservation chamber 8. A void is formed within the receiving shell 11 that is delineated by the first wall surface 12 and the second wall surface 13; this is the receiving cavity 15. Atop the receiving shell 11 is the lock indication arrow 42, which should be directed towards the preservation chamber 8. The third locking receptacle 14 should traverse through the first wall surface 12 into the receiving cavity 15.

Generally, the first recessed surface 7 is a grooved portion of the structure of the cryopreservation device 1 that can accept the embodiment of the base attachment 2. The first surface 5 is oppositely positioned to the second surface 6; furthermore, the first recessed surface 7 is concentrically positioned on the second surface 6. The first locking receptacle 16, the second locking receptacle 17, and the third locking receptacle 14 are integral components of the mechanical locking system. These components allow the base attachment 1 to be semi-permanently attached to the cryopreservation device 1. The first locking receptacle 16 and the second locking receptacle 17 traverse through the first surface 5 and the first recessed surface 7. Each receptacle allows a spring-loaded locking mechanism to be inserted through its opening. Also traversing the first surface 5 and the first recessed surface 7 are the plurality of latching receptacles 18. Beneath each of the plurality of latching receptacles 18 are each of the plurality of clips 19. The plurality of clips 19 is connected to the second surface 6. A gap should be formed between the clips 19 and the first recessed surface 7 so that a card, label or tag can be inserted. A tool, or narrow object, should be able to traverse through a latching receptacle 18 so that such cards, labels, or tag should can be withdrawn. If the plurality of clips 19 has a flexural structure, then they should be able to be bent so that the cards, labels or tags could be withdrawn more easily. However, the plurality of clips 19 may be replaced with any similarly functioning technology that maintains such conventional tracking and recording methods, and the present invention should not be limited to solely using a plurality of clips 19.

As is shown by FIG. 5 and FIG. 11-FIG. 13, the base attachment 2 comprises a first spring-loaded barb 20, a second spring-loaded barb 21, a first base surface 23, an electronics encasement 25, a first recessed clip groove 22, a second recessed clip groove 45, and a third recessed clip groove 46. The integrated electronics system 3 is embedded within the electronics encasement 25. The electronics encasement 25 is positioned atop the first base surface 23, wherein the electronics encasement 25 further comprises a first encasement wall 26, a second encasement wall 27, a third spring-loaded barb 28, and an encasement cavity 29. The first spring-loaded barb 20, the second spring-loaded barb 21, and the third spring-loaded barb 28 are also integral components of the mechanical locking system. The first spring-loaded barb 20 and the second spring-loaded barb 21 are positioned atop the first base surface 23, opposite to the electronics encasement 25—the first spring-loaded barb 20 is adjacent to the second spring-loaded barb 21. Between the first spring-loaded barb 20 and the second spring-loaded barb 21 is the first recessed clip groove 22. The second recessed clip groove 45 is positioned adjacently to the electronics encasement. The third recessed clip groove 46 is positioned adjacently to the electronics encasement as well, oppositely to the second recessed clip groove 45. The first recessed clip groove 22, the second recessed clip groove 45, and the third recessed clip groove 46 are recessed portions of the first base surface 23 that enables the base attachment 2 to avoid obstruction with the plurality of clips 19 on the cryopreservation device 1. Positioned on the first encasement wall 26 is the third spring-loaded barb 28. In essence, the first spring-loaded barb 20 and the second spring-loaded barb 21 are used to secure the first base surface within the first recessed surface 7, while the third spring loaded barb 28 is used to secure the electronics encasement 25 within the receiving shell 11. It is assumed that each of the spring-loaded barbs is compressive.

As aforementioned, the mechanical locking system keeps the cryopreservation device 1 semi-permanently connected to the base attachment 2. This is provided through the connections between the first spring-loaded barb 20 and the first locking receptacle 16, the second spring-loaded barb 21 and the second locking receptacle 17, the third spring loaded barb 28 and the third locking receptacle 14. Each spring-loaded barb behaves similarly and should have a greater surface area in their decompressed state than the openings of each of the locking receptacles. As the base attachment 2 is fitted into the first recessed surface 7 of the cryopreservation device 1, each spring-loaded barb should compress while attempting to traverse through each of the locking receptacles. Specifically, the first spring-loaded barb 20 should compress to fit through the opening of the first locking receptacle 16; the second spring-loaded barb 21 should compress to fit through the opening of the second locking receptacle 17; and, the third spring-loaded barb 28 should compress to fit through the opening of the third locking receptacle 14. After the spring-loaded barbs have fully exited the locking receptacles, the lack of a compressive force should rapidly return the spring-loaded barbs to its decompressed state. Since the decompressed state of the locking barbs has a greater surface area than the locking receptacles, the base attachment 2 should become secured to the cryopreservation device 1. A special tool may be needed to detach the cryopreservation device 1 from the base attachment 2 because multiple spring-loaded barbs are positioned non-uniformly on the base attachment 2.

In order to detach the cryopreservation device 1 from the base attachment 2, each of the spring-loaded barbs must be synchronously compressed and then the base attachment 2 must be grasped and pulled. The entirety of the spring-loaded barbs must be compressed enough so that each spring-loaded barbs can traverse through openings of the locking receptacles. If only a portion of the spring-loaded barbs are sufficiently compressed, then it's possible that the base attachment 2 will be unable detach from the cryopreservation device 1. It is important to keep the cryopreservation device 1 secured to the base attachment 2 because this strengthens the validity of the data acquired by the integrated electronics system 3—the acquired data should always coincide with the specimens preserved by the cryopreservation device 1. The base attachment 2 may also have a flexible structure than can assist the separation of the base attachment 2 from the cryopreservation device 1.

It should be known that the base attachment 2 could be secured or removed from the cryopreservation device 1 through numerous mechanical or electrical locking systems and the present invention should not be limited to the aforementioned attaching and removal system. However, using spring-loaded barbs and locking receptacles is more cost-effective and simple to operate with minimal risk of failure.

Figure 1:
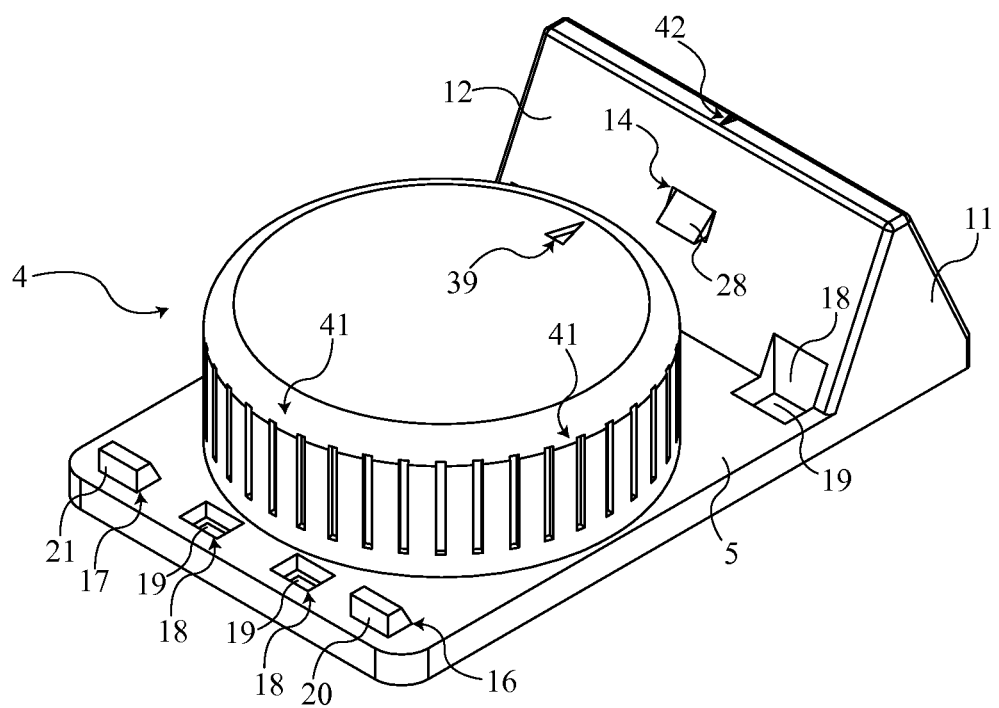
FIG. 1 is a perspective view of the present invention, showing the present invention fully configured.
Figure 2:
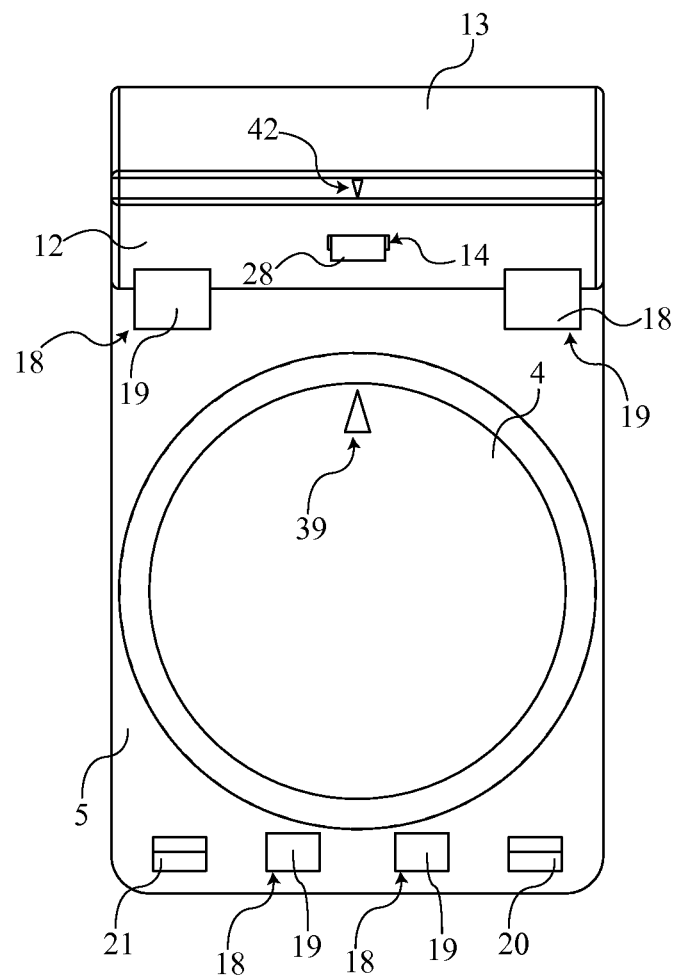
FIG. 2 is a top view of the present invention, showing the present invention fully configured.
Figure 3:
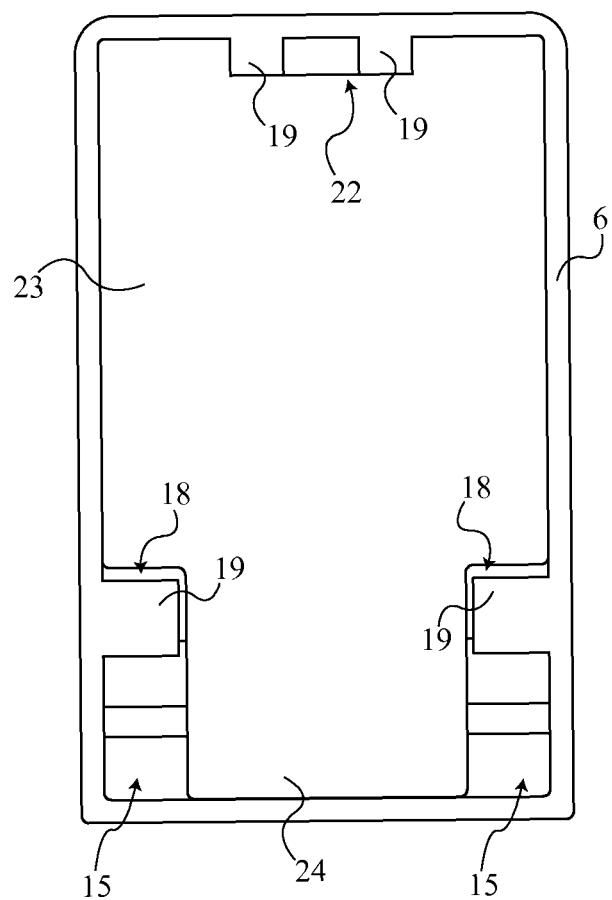
FIG. 3 is bottom view of the present invention, showing the present invention fully configured.
Figure 4:
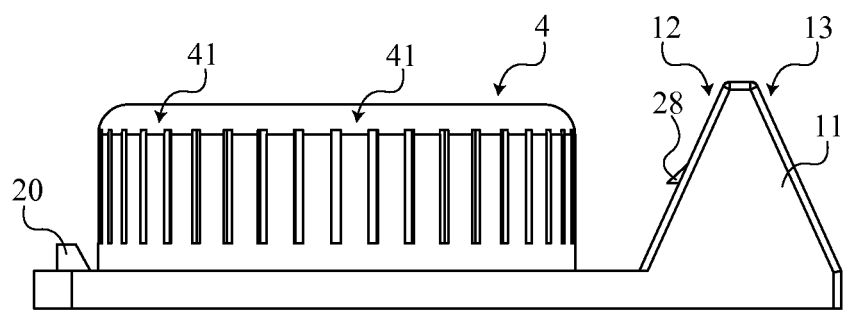
FIG. 4 is a right side view of the present invention, showing the present invention fully configured.
Figure 5:
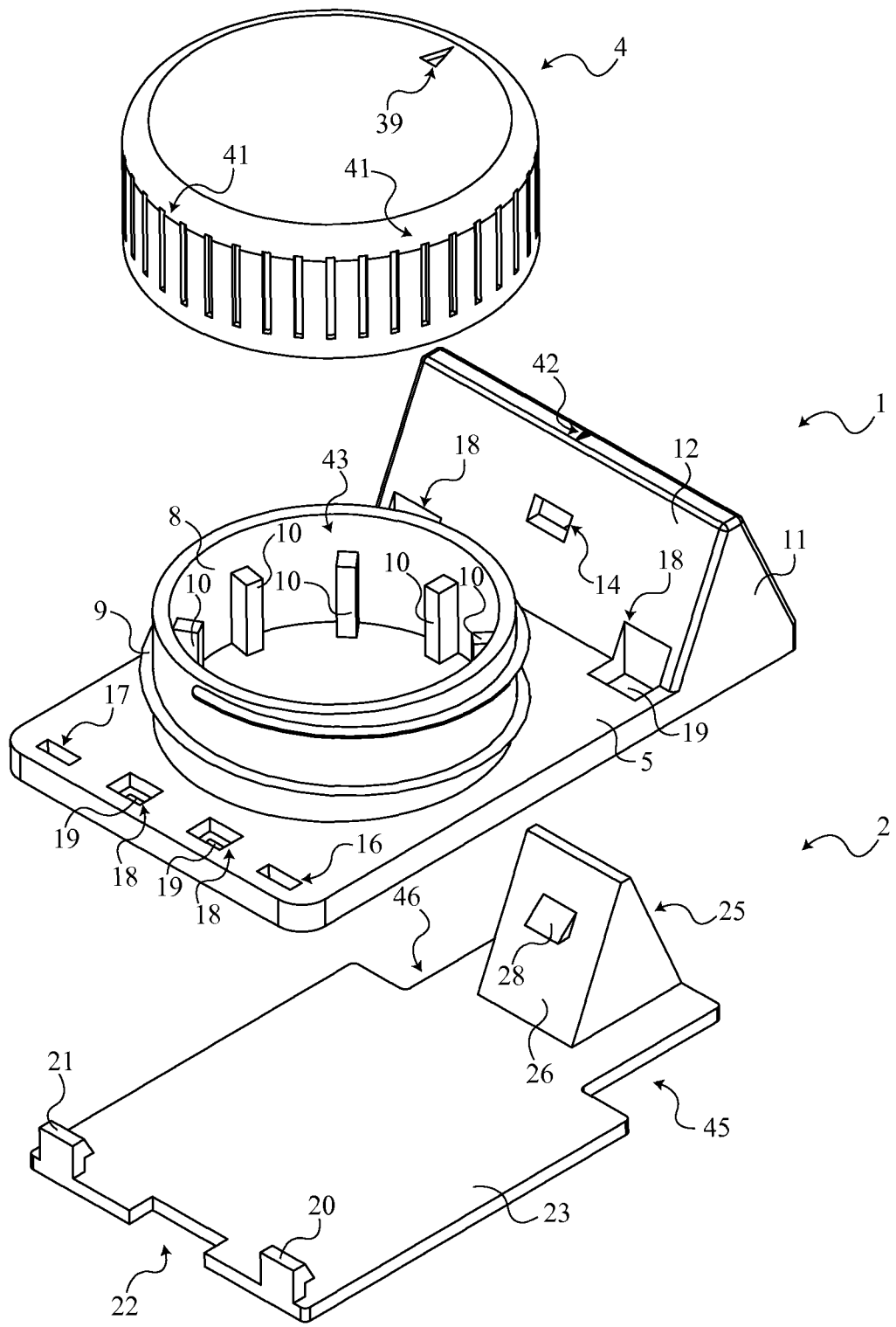
FIG. 5 is an exploded view of the present invention.
Figure 6:
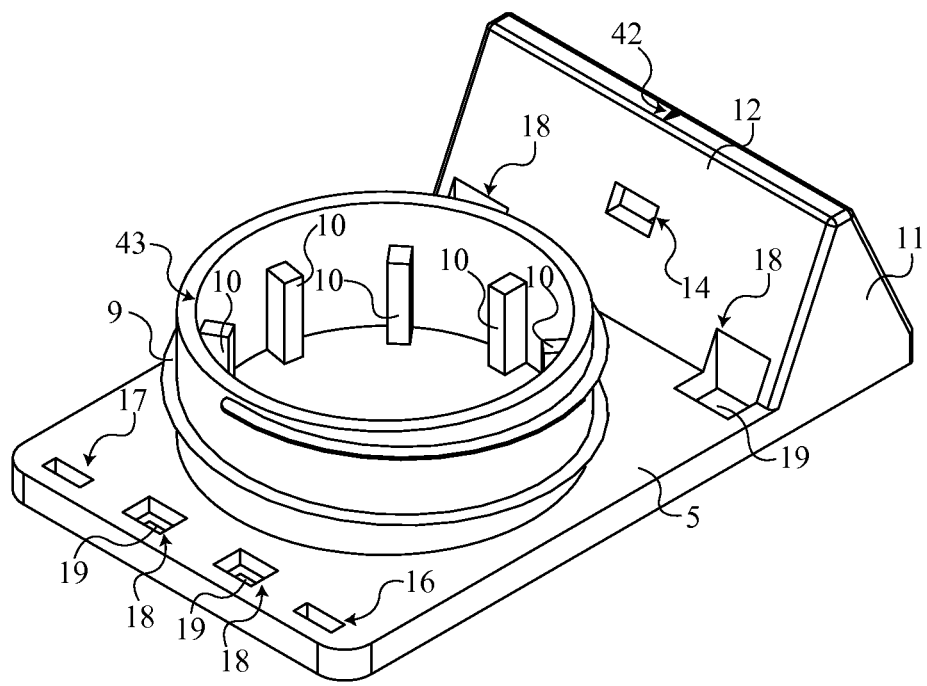
FIG. 6 is a perspective view of the cryopreservation device.
Figure 7:
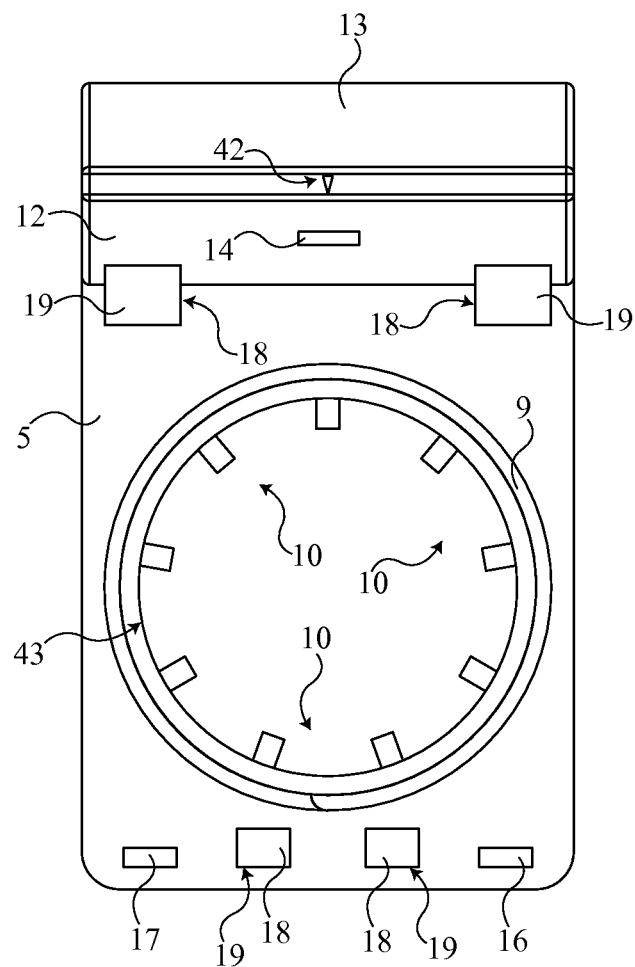
FIG. 7 is a top view of the cryopreservation device.
Figure 8:
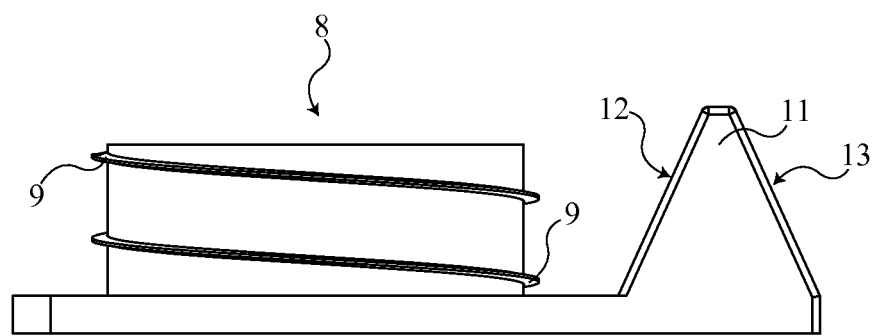
FIG. 8 is a right side view of the cryopreservation device.
Figure 9:
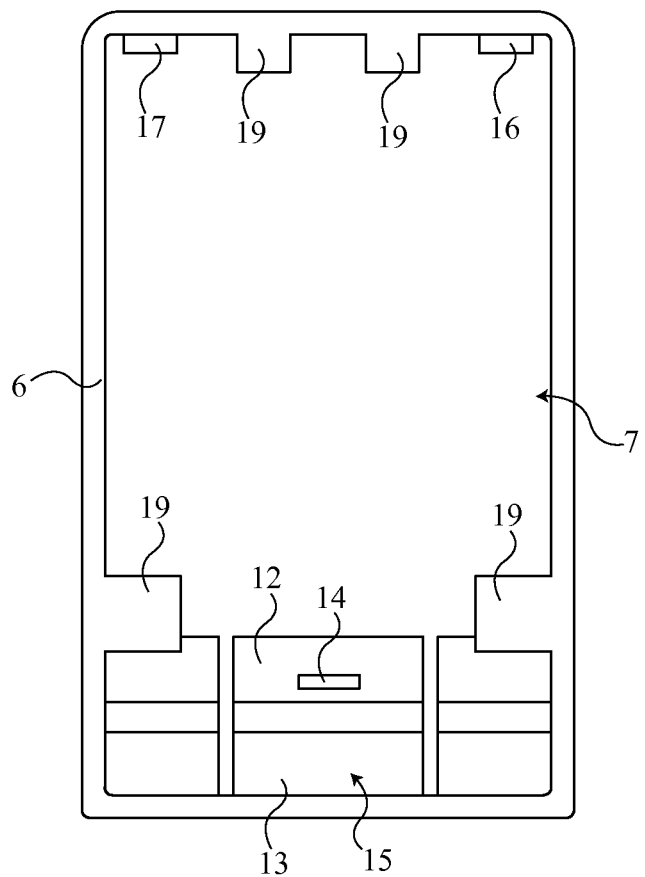
FIG. 9 is a bottom view of the cryopreservation device.
Figure 10:
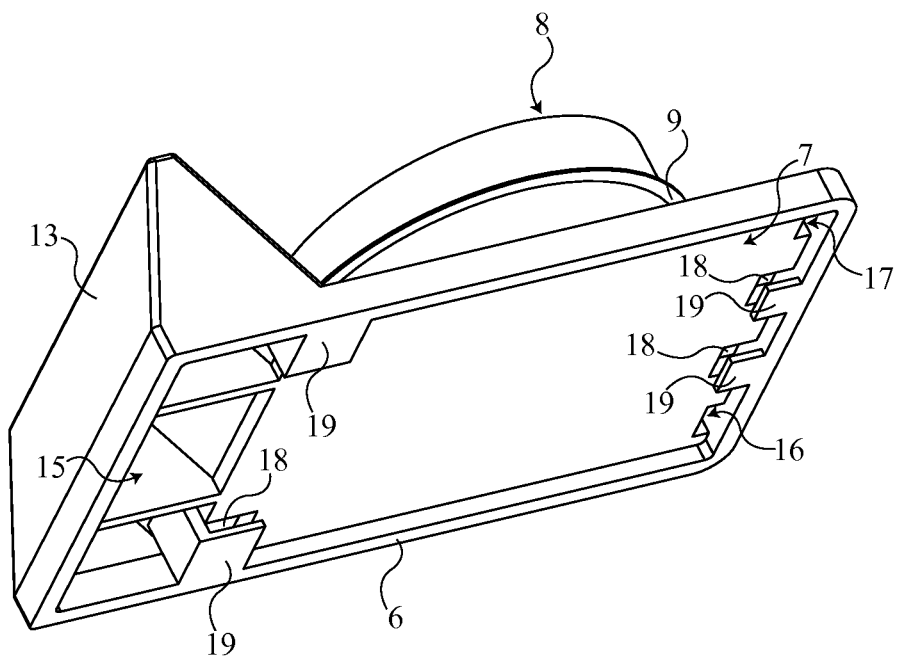
FIG. 10 is a rear perspective view of the cryopreservation device.
Figure 11:
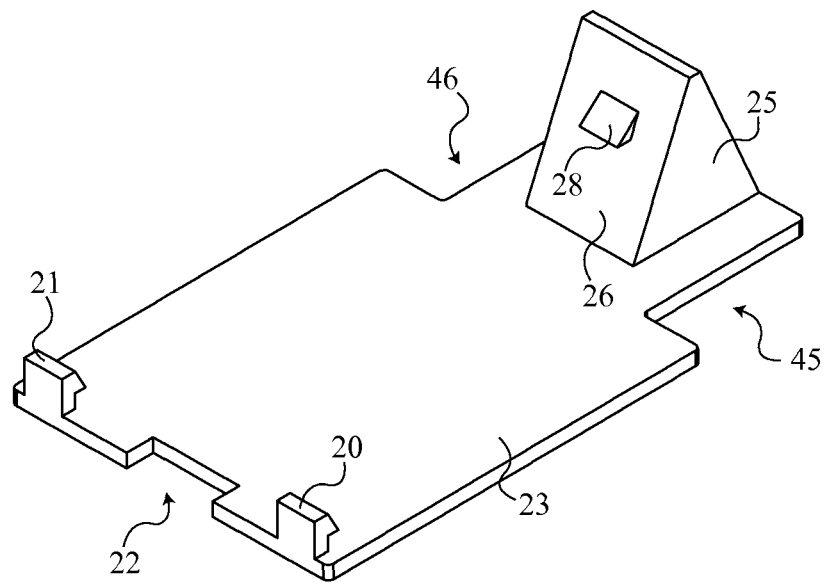
FIG. 11 is a perspective view of the base attachment.
Figure 12:
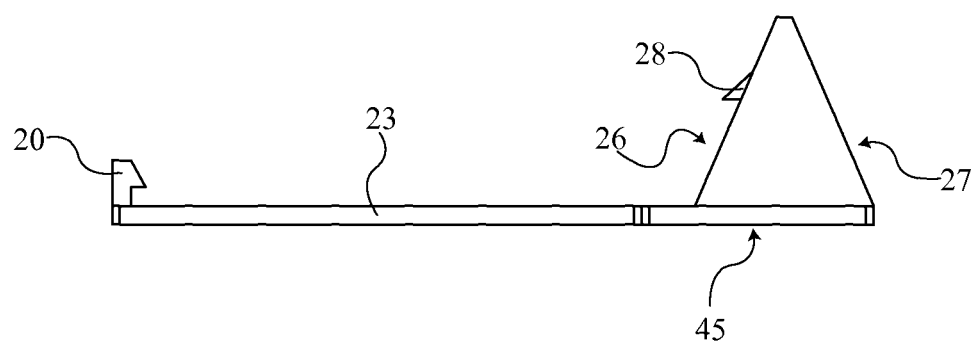
FIG. 12 is a right side view of the base attachment.
Figure 13:
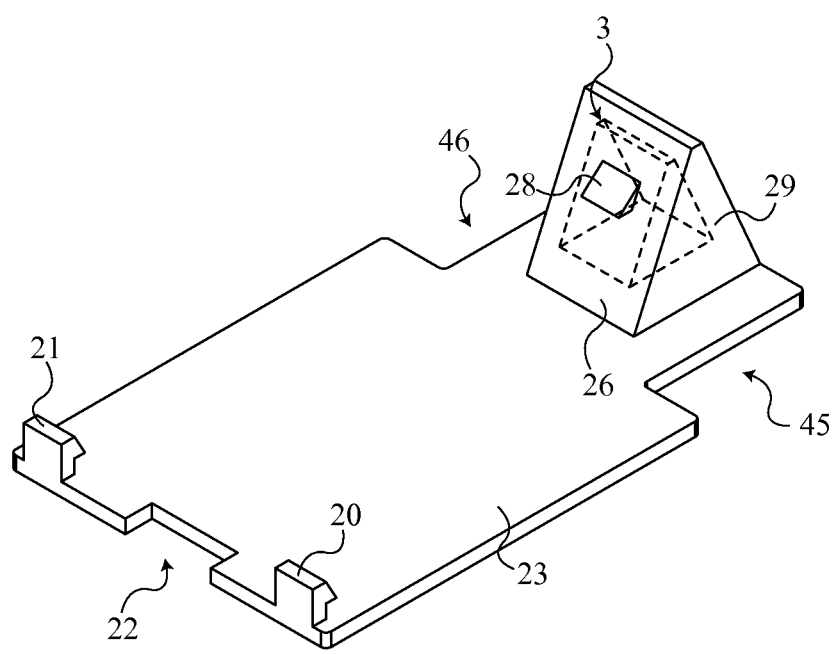
FIG. 13 is a perspective view of the base attachment, showing the integrated electronics system.
Figure 14:
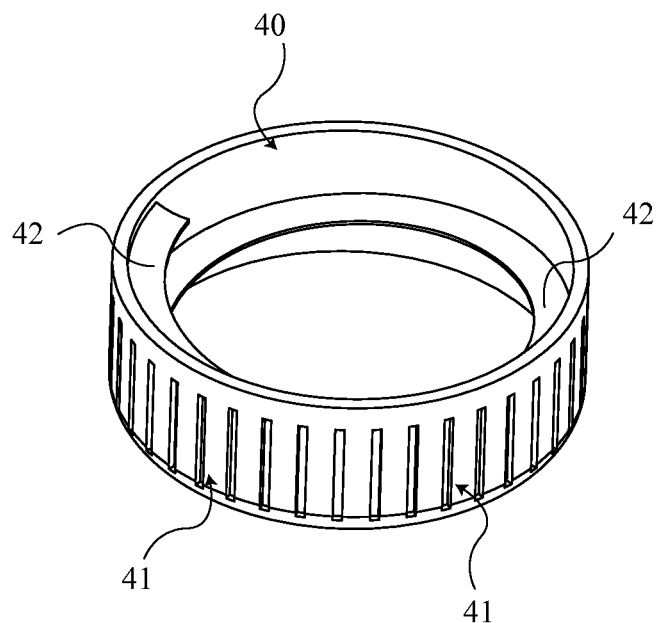
FIG. 14 is a bottom perspective view of the sealing cap.

As is shown by FIG. 5 and FIG. 14, the sealing cap 4 comprises a locking arrow 39, a cap cavity 40, a cap thread 42, and a plurality of gripping grooves 41. The sealing cap 4 encloses the preservation chamber 8, restricting the innards of the preservation chamber 8 from the outside environment. The preferred embodiment of the sealing cap 4 is a screw-on cap that is rotated to tighten and seal to another object. The cap thread 42 provides the sealing capability and should be located within the cap cavity 40. The sealing cap 4 tightens and seals to the preservation chamber 8 by engaging the cap thread 42 with the chamber thread 9. Preferably, the cap thread 42 is helical so that it can be locked onto the preservation chamber 8 by rotating or twisting the sealing cap 4. The sealing cap 4 should be adequately distanced from the preservation chamber 8 to compensate for thermal expansion and contraction between the sealing cap 4 and the preservation chamber 8. The structure of the preservation chamber 8 and the sealing cap 4 will expand if brought into a warmer environment from the cryogenic environment. This situation may permanently lock the sealing cap 4 to the preservation chamber 8 if thermal expansion and contraction is not accounted for. The locking arrow 39 is positioned atop the sealing cap 4 in order to indicate when sealing cap 4 is fully sealed. The locking arrow 39 should be directed towards the lock indication arrow 42 once the sealing cap 4 is fully tightened. Moreover, the lock indication arrow 42 and the indication arrow are for convenience. When the sealing cap 4 is fully tightened to the preservation chamber 8, the preservation chamber 8 should be enclosed within the cap cavity 40. Each of the plurality of gripping grooves 41 is circumferentially positioned around the sealing cap 4. Basically, these are grooves that increase the sealing cap's 4 ability to be gripped when it is tightened or loosened. Since the present invention will mostly reside within a cryogenic environment, the embodiment of the sealing cap 4 may become very smooth, making it difficult to release the cap from the from the preservation chamber 8. Handling the sealing cap 4 can be difficult within the cryogenic environment because thick insulated gloves must be worn. Therefore, the sealing cap 4 can be more easily detached from the preservation chamber 8 by handling and rotating the sealing cap 4 by the gripping grooves 41.

Although the invention has been explained in relation to its preferred embodiment, it is to be understood that many other possible modifications and variations can be made without departing from the spirit and scope of the invention as hereinafter claimed.

What is claimed is:
1. A retrofitted electronic track device for use with cryopreservation device comprising:
 a cryopreservation device;
 a base attachment;
 an integrated electronics system;
 a sealing cap;
 the cryopreservation device comprises a first surface, a second surface, a first recessed surface, a preservation chamber, a receiving shell, a first locking receptacle, a second locking receptacle, a plurality of latching receptacles, and a plurality of clips;
 the base attachment comprises a first spring loaded barb, a second spring loaded barb, a first recessed clip groove, a second recessed clip groove, a third recessed clip groove, a first base surface, and an electronics encasement;

the integrated electronics system comprises an energy source, a plurality of sensors, a data storage device, a time recording device, a control block, and a communication device;

the sealing cap comprises, a locking arrow, a cap cavity, a cap thread, and a plurality of gripping grooves;

the preservation chamber comprises a chamber thread, a plurality of inner splines, and a chamber cavity;

the receiving shell comprises a first shell wall, a second shell wall, a third locking receptacle, and a receiving cavity;

the electronics encasement comprises a first encasement wall, a second encasement wall, a third spring loaded barb, and an encasement cavity;

the preservation chamber being enclosed by the sealing cap;

the cap thread being engaged with the chamber thread;

the cryopreservation device being removably attached to the base attachment through the first spring-loaded barb, the second spring-loaded barb, the third spring-loaded barb, the first locking receptacle, the second locking receptacle, and the third locking receptacle;

the first locking receptacle being traversed by the first spring-loaded barb;

the second locking receptacle being traversed by the second spring-loaded barb;

the third locking receptacle being traversed by the third spring-loaded barb;

the electronics encasement being affixed within the encasement cavity;

the first base surface being affixed within the first recessed surface;

each of the plurality sensors, the energy source, the data storage device, the time recording device and the communication device being electrically connected to the control block; and the integrated electronics system being embedded within the encasement cavity.

2. A retrofitted electronic tracking and recording device for use with a cryopreservation device as claimed in claim 1 further comprising:

the first surface being positioned oppositely to the second surface;

the first recessed surface being concentrically positioned on the second surface;

the preservation chamber being positioned atop the first surface;

the receiving shell being positioned atop the first surface;

the receiving shell being positioned adjacently to the preservation chamber;

the plurality of latching receptacles traversing both the first surface and the first recessed surface;

each of the plurality of clips being positioned on the second surface, beneath each of the plurality of latching receptacles;

the first locking receptacle and the second locking receptacle both traversing through the first surface and the first recessed surface; and the first locking receptacle being positioned adjacently to the second locking receptacle.

3. A retrofitted electronic tracking and recording device for use with a cryopreservation device as claimed in claim 1 further comprising:

the chamber cavity being concentrically positioned atop the preservation chamber;

the plurality of inner splines being circumferentially positioned within the chamber cavity; and the chamber being enwrapped by the chamber thread.

4. A retrofitted electronic tracking and recording device for use with a cryopreservation device as claimed in claim 1 further comprising:

the receiving cavity traversing through the first recessed surface into the receiving shell;

the receiving cavity being delineated by the first wall surface, the second wall surface, and the first recessed surface;

the first wall surface being positioned oppositely to the second wall surface;

the third locking receptacle being positioned on the first wall surface; and the third locking receptacle traversing through the first wall surface into the receiving cavity.

5. A retrofitted electronic tracking and recording device for use with a cryopreservation device as claimed in claim 4 further comprising:

a lock indication arrow;

the lock indication arrow being positioned atop the receiving shell, between the first wall surface and the second wall surface; and the lock indication arrow being directed towards the center of the preservation chamber.

6. A retrofitted electronic tracking and recording device for use with a cryopreservation device as claimed in claim 1 further comprising:

the cap cavity being concentrically positioned below the sealing cap;

the cap thread being helically positioned within the cap cavity; and the sealing cap being enwrapped by the plurality of gripping grooves.

7. A retrofitted electronic tracking and recording device for use with a cryopreservation device as claimed in claim 6 further comprising:

a lock arrow; and the lock arrow being positioned atop the sealing cap, opposite to the cap cavity.

8. A retrofitted electronic tracking and recording device for use with a cryopreservation device as claimed in claim 1 further comprising:

the first spring-loaded barb being positioned atop the first base surface;

the second spring-loaded barb being positioned atop the first base surface, adjacent to the first spring-loaded barb;

the electronics encasement being positioned atop the first base surface;

the first encasement wall being positioned oppositely to the second encasement wall;

the third spring-loaded barb being positioned on the first encasement wall;

the encasement cavity being delineated by the first encasement wall, the second encasement wall, and the second base surface;

the first recessed clip groove being positioned between the first spring-loaded barb and the second spring-loaded barb;

the second recessed clip groove being positioned adjacently to the electronics encasement; and the third recessed clip groove being positioned adjacently to the electronics encasement, opposite to the second recessed clip groove.

9. A retrofitted electronic tracking and recording device for use with a cryopreservation device comprising:
a cryopreservation device;
a base attachment;
an integrated electronics system;
a sealing cap;
the cryopreservation device comprises a first surface, a second surface, a first recessed surface, a preservation chamber, a receiving shell, a first locking receptacle, a second locking receptacle, a plurality of latching receptacles, and a plurality of clips;
the base attachment comprises a first spring loaded barb, a second spring loaded barb, a first recessed clip groove, a second recessed clip groove, a third recessed clip groove, a first base surface, and an electronics encasement;
the integrated electronics system comprises an energy source, a plurality of sensors, a data storage device, a time recording device, a control block, and a communication device;
the sealing cap comprises, a cap cavity, a cap thread, and a plurality of gripping grooves;
the preservation chamber comprises a chamber thread, a plurality of inner splines, and a chamber cavity;
the receiving shell comprising a first shell wall, a second shell wall, a third locking receptacle, and a receiving cavity;
wherein the cap thread is engaged with the chamber thread;
the electronics encasement comprises a first encasement wall, a second encasement wall, a third spring loaded barb, and an encasement cavity;
each of the plurality of sensors, the energy source, the data storage device, the time recording device and the communication device being electronically connected to the control block;
the integrated electronics system being embedded within the encasement cavity; and
the cryopreservation device being removably attached to the base attachment through the first spring-loaded barb, the second spring-loaded barb, the third spring-loaded barb, the first locking receptacle, the second locking receptacle, and the third locking receptacle;
the preservation chamber being enclosed by the sealing cap;
the first locking receptacle being traversed by the first spring loaded barb;
the second locking receptacle being traversed by the second spring loaded barb;
the third locking receptacle being traversed by the third spring loaded barb; and
the first base surface being affixed within the first recessed surface.

10. A retrofitted electronic tracking and recording device for use with a cryopreservation device as claimed in claim 9 further comprising:
the first surface being positioned oppositely to the second surface;
the first recessed surface being concentrically positioned on the second surface;
the preservation chamber being positioned atop the first surface;
the receiving shell being positioned atop the first surface;
the receiving shell being positioned adjacently to the preservation chamber;
the plurality of latching receptacles traversing both the first surface and the first recessed surface;
each of the plurality of clips being positioned on the second surface, beneath each of the plurality of latching receptacles;
the first locking receptacle and the second locking receptacle both traversing through the first surface and the first recessed surface; and
the first locking receptacle being positioned adjacently to the second locking receptacle.

11. A retrofitted electronic tracking and recording device for use with a cryopreservation device as claimed in claim 9 further comprising:
the chamber cavity being concentrically positioned atop the preservation chamber;
the plurality of inner splines being circumferentially positioned within the chamber cavity; and
the chamber being enwrapped by the chamber thread.

12. A retrofitted electronic tracking and recording device for use with a cryopreservation device as claimed in claim 9 further comprising:
the receiving cavity traversing through the first recessed surface into the receiving shell;
the receiving cavity being delineated by the first wall surface, the second wall surface, and the first recessed surface;
the first wall surface being positioned oppositely to the second wall surface;
the third locking receptacle being positioned on the first wall surface; and
the third locking receptacle traversing through the first wall surface into the receiving cavity.

13. A retrofitted electronic tracking and recording device for use with a cryopreservation device as claimed in claim 12 comprising:
a lock indication arrow;
the lock indication arrow being positioned atop the receiving shell, between the first wall surface and the second wall surface; and
the lock indication arrow being directed towards the center of the preservation chamber.

14. A retrofitted electronic tracking and recording device for use with a cryopreservation device as claimed in claim 9 further comprising:
the cap cavity being concentrically positioned below the sealing cap;
the cap thread being helically positioned within the cap cavity; and
the sealing cap being enwrapped by the plurality of gripping grooves.

15. A retrofitted electronic tracking and recording device for use with a cryopreservation device as claimed in claim 14 further comprising:
a lock arrow; and
the lock arrow being positioned atop the sealing cap, opposite to the cap cavity.

16. A retrofitted electronic tracking and recording device for use with a cryopreservation device as claimed in claim 9 further comprising:
the first spring-loaded barb being positioned atop the first base surface;
the second spring-loaded barb being positioned atop the first base surface, adjacent to the first spring-loaded barb;
the electronics encasement being positioned atop the second base surface;
the first encasement wall being positioned oppositely to the second encasement wall;

the third spring-loaded barb being positioned on the first encasement wall;

the encasement cavity being delineated by the first encasement wall, the second encasement wall, and the second base surface;

the first recessed clip groove being positioned between the first spring-loaded barb and the second spring-loaded barb;

the second recessed clip groove being positioned adjacently to the electronics encasement; and the third recessed clip groove being positioned adjacently to the electronics encasement, opposite to the second recessed clip groove.

\* \* \* \* \*